United States Patent [19]

Hasegawa

[11] 4,201,866
[45] May 6, 1980

[54] O-HEMI-SUCCINATE OF PROPRANOLOL

[75] Inventor: Jun Hasegawa, Clinton, N.Y.

[73] Assignee: American Home Products Corporation, New York, N.Y.

[21] Appl. No.: 859,628

[22] Filed: Dec. 12, 1977

Related U.S. Application Data

[63] Continuation-in-part of Ser. No. 759,947, Jan. 17, 1977, abandoned.

[51] Int. Cl.$^2$ ............................................. C07C 69/40
[52] U.S. Cl. ..................................... 560/194; 424/313
[58] Field of Search ........................................ 560/194

[56] References Cited

U.S. PATENT DOCUMENTS

| | | | |
|---|---|---|---|
| 3,337,628 | 8/1967 | Crowther et al. | 260/570.7 |
| 4,026,879 | 5/1977 | Spector | 260/121 |

OTHER PUBLICATIONS

Kawashima et al., Jour. Pharmacology and Experimental Therapeutics, 196 (2) 517–523 (1976).
Nadean et al., Can. Society Clinical Pharmacology, p. 657A, Jan., 1977.

*Primary Examiner*—Jane S. Myers
*Attorney, Agent, or Firm*—Adley F. Mandel

[57] ABSTRACT

This invention is directed to novel compounds having β-adrenergic blocking activity. The compounds are represented by the following structural formula:

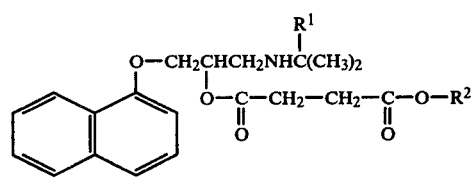

wherein $R^1$ is hydrogen or methyl, $R^2$ is hydrogen or lower alkyl and their pharmaceutically acceptable salts.

1 Claim, No Drawings

O-HEMI-SUCCINATE OF PROPRANOLOL

This application is a continuation-in-part of Ser. No. 759,947, filed Jan. 17, 1977, now abandoned.

BACKGROUND OF THE INVENTION

1. Field of the Invention

This invention relates to derivatives of butanedioic acid. More particularly this invention relates to compounds having the formula

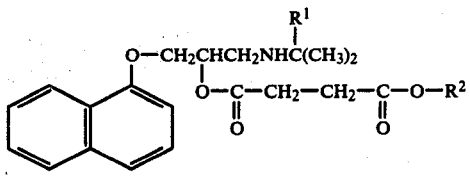

wherein $R^1$ is hydrogen or methyl, $R^2$ is hydrogen or lower alkyl and their pharmaceutically acceptable salts. These compounds have β-adrenergic blocking activity.

2. Description of the Prior Art

U.S. Pat. No. 3,337,628 describes 1-isopropyl-amino-3-(1-naphthoxy)-2-propanol (propranolol). This compound or the pharmaceutically acceptable salt of this compound can be used as the precursor in the synthesis of one of the presently claimed compounds. Additionally, U.S. Pat. No. 3,337,628 discloses that propranolol can be used in the treatment of coronary artery disease and specifically as a β-adrenergic blocking agent. However, a major drawback of compounds disclosed in U.S. Pat. No. 3,337,628 and particularly propranolol is that because of extensive metabolism, little unchanged active material reaches the systemic circulation after oral administration. Additionally, plasma levels of propranolol show a large patient to patient variation.

The prior art contains the following theories as to the disposition of propanolol when taken orally:

1. Substantial amounts of propanolol are converted to the glucoronide during the absorption process and enters enterohepatic circulation.
2. Free propranolol absorbed from the G.I. Tract into the portal vein is distributed in the liver depending on the absorption rate and the dose of propanolol. Matabolites formed in the liver are probably converted to the conjugated glucuronide form.
3. Conjugated propranolol is not excreted rapidly into the urine. The major part of the conjugated form of propranolol is excreted in bile. Although the detailed process of the fate of the conjugated propranolol excreted in bile, is not known it might be reasonable to assume the following steps.
   (1) The bile is concentrated at the gall bladder, the conjugated propranolol is partially absorbed from bile into the systemic circulation.
   (2) Most of the glucuronide is excreted into the G.I. Tract, probably hydrolyzed by enzymatic action and reabsorbed. The enterohepatic circulation of propranolol constitutes a hidden depot in the body.
4. The metabolites are excreted in urine as conjugated forms.

It has now been discovered that the extent of the above forms of metabolism in the G.I. tract and/or the liver can be markedly reduced when the compounds of this invention are employed. While not wishing to be bound by any theory, it is believed that the compounds of this invention are especially effective since they protect the β-adrenergic blocking compound from extensive metabolism during absorption and are rapidly hydrolyzed after absorption to release the active compound into the blood.

SUMMARY OF THE INVENTION

This invention relates to the following novel compounds and their pharmaceutically acceptable salts

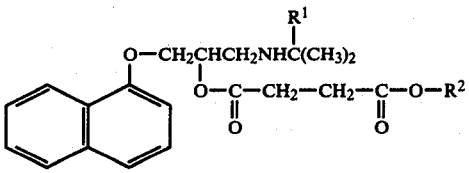

wherein $R^1$ is hydrogen or methyl and $R^2$ is hydrogen or lower alkyl. The use of these compounds improve the bioavailability of the β-adrenergic compound and reduces variation in plasma levels.

DESCRIPTION OF THE INVENTION

The term lower alkyl encompasses straight chain alkyl groups containing from 1 to 3 carbon atoms.

The preferred compounds of this invention are the hydrochloride salts of the above-described compounds. The preferred compound is propranolol-o-hemi-succinate HCl.

The compounds of this invention, when $R^2$ is hydrogen, can be prepared in the following manner: The hydrochloride salt of

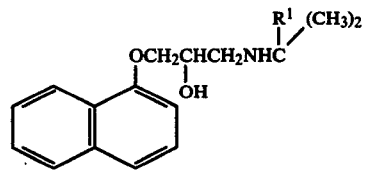

and succinic anhydride or succinic acid are refluxed in toluene or any other suitable non-basic solvent for approximately 1 to about 10 hours and preferably from about 3 to 7 hours. The O-hemisuccinate ester separates as an oil during the reaction. The solvent is decanted and the product is crystallized from acetone. The compounds of this invention, when $R^2$ is lower alkyl, is prepared in a similar manner but starting with a halo succinic ester.

As will be understood by those skilled in the art the compounds of this invention may be utilized in their basic form or in the form of the therapeutically-active salts thereof, e.g. the hydrochloride salt etc.

As will be also understood by those skilled in the art, the compounds of the invention may be utilized in suitable dosage form, including solutions, suspensions, tablets, capsules, and the like.

The following examples are illustrative of the invention.

EXAMPLE I

Butanedioic Acid Monol[[2-(1-Methylethyl] Amino]-1-[(1-Naphthalenyloxy) Methyl] Ethyl] Ester Hydrochloride ($R^1$ and $R^2$ are hydrogen) was prepared in the following manner.

5.g of propranolol hydrochloride (1 eq.) and 2.0 g of succinic anhydride (1 eq.) was refluxed in toluene for 5 hrs. The newly-formed product separated as an oil during the reaction. The toluene was decanted and the product was crystallized from acetone.

Anal. Calcd. for $C_{20}H_{26}ClNO_5$: C, 60.67; H, 6.61; N, 3.53%. Found: C, 60.97; H, 6.96; N, 3.51%. Melting: Point 112°–114° C.

EXAMPLE 2

1. Oral administration of propranolol-o-hemi-succinate HCl and Propranolol HCl

In this experiment, four beagle dogs were given an 80 mg. oral dose of propranolol HCl or an equivalent dose of the o-hemi-succinate. The animals were divided into two groups of two, each group receiving the drugs according to a crossover design. The crossover experiment was repeated twice. A period of at least one week elapsed between each dosing day. Blood samples were obtained at regular intervals after dosing a plasma was analyzed for free propranolol concentrations.

Plasma was analyzed for free propranolol by a TLC fluorometric procedure. Two ml samples were mixed with 2 ml of pH 10 buffer and extracted with 25 ml of ethyl ether. A 20 ml aliquot from the ether phase was evaporated to dryness and the dry residue was dissolved in 100 μl of ethanol. Twenty-five μl aliquots were spotted on TLC plates of silica gel along with standard solutions of propranolol. The plates were developed in a saturated tank containing the solvent system methanol (100 ml): concentrated $NH_4OH$ (0.4 ml). After development, the plates were dried and sprayed with a 50% solution of propylene glycol in water. They were then read in the fluorescence mode of a Schoeffel spectrodensitometer. The limit of reliable quantitation was 2 ng. of propranolol per ml of plasma.

Plasma levels of free propranolol after oral doses of propranolol hydrochloride and the succinate are given in Tables I and II respectively. Plasma level of propranolol were considerably higher following oral administration of the o-hemi-succinate. The average AUC's (0–6 hr.) for the overall study were 1075 after the o-hemi-succinate and 132 after propranolol (Table I and II). Moreover, fluctuation in plasma levels were reduced by 35% following administration of the pro-drug, as revealed by the AUC values.

Absorption of the succinate and its conversion to propranolol were rapid, peak plasma levels of propranolol being reached between ½ to 1 hour after administration. The half-life of propranolol was virtually the same after administration of either the pro-drug (1.7 hours) or propranolol (1.8 hours). Hence, it can be seen that the plasma levels of free propranolol were eight times higher with the o-hemi-succinate than those obtained from an equivalent dose of propranolol hydrochloride.

TABLE I

| | Dog # | Time After Dosing | | | | | | AUC ng/ml . hr |
|---|---|---|---|---|---|---|---|---|
| | | 0 | ½ hr | 1 hr | 2 hr | 4 hr | 6 hr | 0–6 hr |
| Study 1 | 159 | 0 | trace | trace | trace | 26 | 17 | 69 |
| | 250 | 0 | 0 | 0 | 23 | 14 | 0 | 63 |
| | 353 | 0 | trace | 11 | 14 | trace | trace | 29 |
| | 1576 | 0 | 53 | 56 | 45 | 12 | trace | 160 |
| | Mean | 0 | 13 | 17 | 21 | 13 | 4 | 81 |
| Study 2 | 159 | 0 | 23 | 31 | 41 | 36 | 21 | 189 |
| | 250 | 0 | 10 | 38 | 51 | 26 | 9 | 171 |
| | 353 | 0 | 103 | 101 | 65 | 33 | 6 | 297 |
| | 1576 | 0 | 24 | 24 | 19 | 17 | 6 | 99 |
| | Mean | 0 | 40 | 48 | 44 | 28 | 10 | 188 |
| | Overall Mean | 0 | 26 | 32 | 32 | 20 | 7 | 132 s.d. 87 C.V. 65% |

Plasma levels (ng/ml) of propranolol in beagle dogs following oral administration of 80 mg of propranolol hydrochloride.

TABLE II

| | Dog # | Time After Dosing | | | | | | AUC ng/ml . hr |
|---|---|---|---|---|---|---|---|---|
| | | 0 | ½ hr | 1 hr | 2 hr | 4 hr | 6 hr | 0–6 hr |
| Study 1 | 159 | 0 | 47 | 143 | 151 | 125 | 90 | 697 |
| | 250 | 0 | 667 | 735 | 269 | 133 | 64 | 1618 |
| | 353 | 0 | 342 | 435 | 214 | 98 | 53 | 1067 |
| | 1576 | 0 | 521 | 205 | 108 | 28 | 19 | 651 |
| | Mean | 0 | 394 | 379 | 186 | 96 | 57 | 1009 |
| Study 2 | 159 | 0 | 627 | 651 | 385 | 156 | 62 | 1753 |
| | 250 | 0 | 125 | 174 | 314 | 94 | 50 | 902 |
| | 353 | 0 | 845 | 456 | 232 | 89 | 31 | 1322 |
| | 1576 | 0 | 459 | 244 | 89 | 25 | 10 | 606 |
| | Mean | 0 | 514 | 381 | 255 | 91 | 38 | 1145 |
| | Overall Mean | 0 | 454 | 380 | 220 | 93 | 47 | 1075 s.d. 445 C.V. 41% |

Plasma levels (ng/ml) of propranolol in beagle dogs following oral administration of a dose of propranolol-o-hemi-succinate equivalent to 80 mg of propranolol hydrochloride.

EXAMPLE 3

Intravenous Administration of Propranolol HCl and Propranolol-o-hemi-succinate HCl In this experiment, the same four dogs used in Example 2 were administered a 20 mg intravenous dose of propranolol HCl on one experimental day and an equivalent dose of the o-hemi-succinate on a second day. A period of one week elapsed between each administration. Blood samples were collected and analyzed as above.

Individual plasma levels of free propranolol following intravenous administration of propranolol HCl and propranolol o-hemi-succinate HCl are shown in Table III.

Conversion of the propranolol ester to propranolol was very fast, high levels of the drug being found only 5 minutes after intravenous administration. Plasma levels of free propranolol were lower following intravenous propranolol o-hemi-succinate-HCl, the average AUC being 369, while it was 746 after-propranolol i.v.

nate hydrochloride (equivalent to 20 mg propranolol HCl). Blood samples were collected at regular intervals after dosing and plasma was analyzed for free propranolol and unchanged propranolol-o-hemi-succinate hydrochloride.

TABLE IV

|  | Dog # | Hours After Dosing | | | | | AUC 0-6 hr ng/ml hr |
|---|---|---|---|---|---|---|---|
|  |  | 0 | ½ | 1 | 2 | 4 | 6 |  |
| Propranolol | 250 | 0 | 10 | 38 | 51 | 26 | 9 | 168 |
|  | 353 | 0 | 18 | 44 | 24 | 7 | 0 | 92 |
| Propranolol-O-hemi-succinate HCl | 250 | 0 | 84 | 42 | 15 | 9 | Trace | 114 |
|  | 353 | 0 | 10 | 50 | 27 | 9 | 0 | 101 |

TABLE III

|  | Dog # | Time After Dosing | | | | | | | | AUC ng/ml . hr 0-6 hr |
|---|---|---|---|---|---|---|---|---|---|---|
|  |  | 0 | 5 min | 10 min | 15 min | ½hr | 1 hr | 2 hr | 4 hr | 6 hr |  |
| Pro- | 159 | 0 | 391 | 368 | 320 | 280 | 240 | 191 | 114 | 53 | 974 |
| prano- | 250 | 0 | 312 | * | 271 | 232 | 207 | 149 | 87 | 45 | 744 |
| lol | 353 | 0 | 376 | 319 | * | 269 | 229 | 119 | 61 | 28 | 615 |
|  | 1576 | 0 | 194 | 177 | 149 | 144 | 128 | 122 | 53 | 39 | 534 |
|  | Mean | 0 | 318 | 288 | 247 | 231 | 201 | 145 | 79 | 41 | 746 |
| Pro- | 159 | 0 | 327 | 229 | 155 | 132 | 83 | 52 | 29 | 17 | 337 |
| pranolol- | 250 | 0 | 289 | 262 | 207 | 191 | 123 | 90 | 36 | 16 | 467 |
| O-hemi- | 353 | 0 | 375 | 262 | 181 | 145 | 86 | 60 | 25 | 18 | 360 |
| succinate | 1576 | 0 | 452 | 310 | 266 | 191 | 87 | 28 | 9 | 0 | 305 |
| HCl | Mean | 0 | 361 | 266 | 202 | 165 | 95 | 58 | 25 | 13 | 369 |

Plasma levels (ng/ml) of propranolol in beagle dogs following intravenous administration of 20 mg of propranolol hydrochloride and an equivalent dose of propranolol-o-hemi-succinate HCl
*Sample lost

EXAMPLE 4

Oral Administration of a Reduced Dose of Propranolol-o-Hemi-Succinate Hydrochloride Two beagle dogs were given an oral dose of 13.4 mg of propranolol-O-hemi-succinate hydrochloride (equivalent to 10 mg. propranolol HCl). Blood samples were obtained at regular intervals after drug administration and plasma analyzed for free propranolol. Plasma levels of free propranolol were compared to those obtained following administration of 80 mg dose of propranolol HCl.

Results are given in Table IV. In dog #353, the AUC's were 101 and 92 after administration of propranolol-O-hemi-succinate hydrochloride and propranolol HCl respectively, in dog #250 the AUC's were 114 and 168. Although only two dogs were tested, results indicate that a dose of propranolol-o-hemi-succinate hydrochloride ⅙ that of propranolol HCl will produce comparable levels of free propranolol in dogs.

EXAMPLE 5

Oral vs Intravenous Administration of propranolol-o-hemi-succinate hydrochloride Four beagle dogs were administered propranolol-o-hemi-succinate hydrochloride either intravenously or orally. The dogs were divided into two groups of two, each group receiving each dosing regimen according to a crossover design. The oral doses consisted of 107 mg of propranolol-o-hemi-succinate hydrochloride (equivalent to 80 mg propranolol HCl) and the intravenous doses consisted of 26.7 mg of propranolol-o-hemi-succi- Plasma levels of free propranolol following oral administration of 80 mg Propranolol HCl and 13.4 mg propranolol-o-hemi-succinate HCl Individual plasma levels of unchanged propranolol-o-hemi-succinate hydrochloride and free propranolol following intravenous and oral administration of propranolol-o-hemi-succinate hydrochloride are given in Table V and Table VI respectively.

Plasma was analyzed for propranolol-o-hemi-succinate hydrochloride by a TLC fluorometric procedure. Two ml samples were mixed with 2 ml of pH 4 buffer and extracted with 40 ml of methylene chloride. A 30 ml aliquot from the organic phase was evaporated to dryness and the residue was dissolved in 100 μl of ethanol. Twenty-five μl aliquots were spotted on TLC plates of silica gel along with standard solutions of propranolol-o-hemi-succinate hydrochloride. The plates were developed in saturated tank containing the solvent system: isopropyl alcohol (55 ml), benzene (40 ml), water (5 ml), formic acid (3 ml). After developement, the plates were dried and sprayed with a 50% solution of propylene glycol in water. They were read in the fluorescence mode of a Schoeffel spectrodensitometer. The limit of reliable quantitation was 25 ng per ml of plasma.

Following intravenous dosing, the t ½ of disappearance of propranolol-o-hemi-succinate hydrochloride was 30 minutes and virtually none of the ester was left 4 hours after administration. The half-life of free propranolol was two hours and significant plasma levels still existed 6 hours after administration of the succinate ester.

TABLE V

| | Dog # | Time After Administration of Pro-Drug | | | | | | | | AUC 0–6 hr 0–6 hr hr. |
|---|---|---|---|---|---|---|---|---|---|---|
| | | 0 | 5 min. | 10 min. | 15 min. | ½hr. | 1 hr. | 2 hrs. | 4 hrs. | 6 hrs. | |
| Levels of | 159 | 0 | 2198 | 1586 | 1213 | 692 | 287 | 91 | 15* | Trace | 1165 |
| Propr- | 250 | 0 | 2773 | 2347 | 1763 | 1134 | 366 | 76 | Trace | Trace | 1534 |
| o-hemi- | 353 | 0 | 2538 | 1785 | 1338 | 811 | — | 132 | Trace | Trace | 1524 |
| suc. | 1576 | 0 | 1433 | 946 | 819 | 487 | 198 | 30 | Trace | Trace | 711 |
| HCl | Mean | 0 | 2235 | 1666 | 1283 | 781 | 284 | 82 | 4* | Trace | 1234 |
| Levels of | 159 | 0 | 231 | 156 | 155 | 108 | 81 | 55 | 28 | 19 | 317 |
| Free | 250 | 0 | 425 | 328 | 215 | 178 | 107 | 84 | 47 | 20 | 486 |
| Pro- | 353 | 0 | 339 | 250 | 166 | 126 | — | 39 | 31 | 9 | 326 |
| pranolol | 1576 | 0 | 210 | 157 | 124 | 118 | 72 | 34 | 21 | 11 | 254 |
| | Mean | 0 | 301 | 223 | 165 | 133 | 65 | 53 | 32 | 15 | 346 |

Plasma levels of propranolol-o-hemi-succinate and free propranolol following intravenous administration of propranolol-o-hemi-succinate.
*Estimate only: below level of reliable quantitation.

TABLE VI

| | Dog # | Time After Administration of Pro-Drug | | | | | AUC 0–6 Hrs. ng/ml Hr. |
|---|---|---|---|---|---|---|---|
| | | 0 | ½Hr. | 1 Hr. | 2 Hrs. | 4 Hrs. | 6 Hrs. | |
| Levels of | 159 | 0 | 140 | 2946 | 715 | 109 | 20* | 3590 |
| Propr- | 250 | 0 | 2443 | 1897 | 390 | 62 | 13* | 3366 |
| o-hem- | 353 | 0 | 3139 | 3239 | 486 | 45 | 0 | 4818 |
| suc. | 1576 | 0 | 1318 | 1323 | 268 | 30 | 8* | 2121 |
| HCl | Mean | 0 | 1760 | 2351 | 465 | 62 | 10* | 3474 |
| Levels of | 159 | 0 | 24 | 409 | 185 | 89 | 51 | 825 |
| Free | 250 | 0 | 527 | 494 | 263 | 111 | 50 | 1300 |
| Pro- | 353 | 0 | 490 | 483 | 190 | 91 | 34 | 1108 |
| propranolol | 1576 | 0 | 220 | 400 | 160 | 76 | 29 | 831 |
| | Mean | 0 | 315 | 447 | 200 | 92 | 41 | 1016 |

Plasma levels of propranolol-o-hemi-succinate and free propranolol following oral administration of propranolol-o-hemi-succinate.
*Estimate only: Below level of reliable quantitation.

EXAMPLE 6

Butanedioic acid-1-[(2-(1-methylethyl)amino] -1-[(1-naphtalenyloxy)methyl] diethylether hydrochloride ($R^1 = H$ and $R^2 = CH_2CH_3$) was prepared in the following manner:

A suspension of propranolol hydrochloride (3g. 10.4 millimoles) and ethyl succinylchloride (3ml, 25.95 millimoles) in dry benzene (6 ml) was refluxed with stirring for 2 hours. The clear solution was evaporated to dryness and the residue twice treated with toluene and reevaporated to dryness (2×75 ml).

The crude product (6.45g) was recrystallized twice from ethylacetatedichloromethane-hexane to yield pure title compound (3.03g. 67%) melting point 91°–93°

| Anal. | | | | |
|---|---|---|---|---|
| Calcd. for | | | | |
| $C_{22}H_{29}NO_5 \cdot HCl$ | C 62.32 | H 7.13, | N 3.30 | |
| Found | | 62.00 | 7.13 | 3.23 |

EXAMPLE 7

The compound of Example 6 was orally administered to beagle dogs in a similar manner as Example 2. Plasma levels of the compound of Example 6 were twice as high as those obtained after an equivalent dose of propranol hydrochloride.

I claim:

1. A compound of the formula

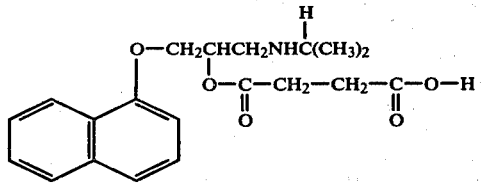

and its pharmaceutically acceptable salts.

* * * * *